United States Patent
Klankermayer et al.

(10) Patent No.: US 9,650,310 B2
(45) Date of Patent: May 16, 2017

(54) METHOD FOR THE METHYLATION OF NITROGEN-CONTAINING ORGANIC COMPOUNDS

(71) Applicant: RHEINISCHE WESTFÄLISCHE TECHNISCHE HOCHSCHULE (RWTH) AACHEN, Aachen (DE)

(72) Inventors: Jürgen Klankermayer, Essen (DE); Kassem Beydoun, Aachen (DE); Thorsten Vom Stein, Köln, DE (US); Walter Leitner, Aachen (DE)

(73) Assignee: RHEINISCHE-WESTFÄLISCHE TECHNISCHE HOCHSCHULE (RWTH) AACHEN (DE)

( * ) Notice: Subject to any disclaimer, the term of this patent is extended or adjusted under 35 U.S.C. 154(b) by 0 days.

(21) Appl. No.: 14/902,704

(22) PCT Filed: Jun. 25, 2014

(86) PCT No.: PCT/EP2014/063343
§ 371 (c)(1),
(2) Date: Jan. 4, 2016

(87) PCT Pub. No.: WO2015/000753
PCT Pub. Date: Jan. 8, 2015

(65) Prior Publication Data
US 2016/0168043 A1    Jun. 16, 2016

(30) Foreign Application Priority Data

Jul. 5, 2013 (EP) .................................... 13175305

(51) Int. Cl.
| | | |
|---|---|---|
| C07C 209/08 | (2006.01) |
| C07C 209/52 | (2006.01) |
| C07C 209/50 | (2006.01) |
| C07C 209/66 | (2006.01) |
| C07C 209/26 | (2006.01) |
| C07C 213/08 | (2006.01) |
| C07C 213/02 | (2006.01) |
| B01J 31/00 | (2006.01) |
| C07C 211/48 | (2006.01) |
| C07C 211/52 | (2006.01) |
| C07C 217/84 | (2006.01) |
| C07B 43/04 | (2006.01) |
| C07D 209/08 | (2006.01) |

(52) U.S. Cl.
CPC ............... C07B 43/04 (2013.01); B01J 31/00 (2013.01); C07C 209/26 (2013.01); C07C 209/50 (2013.01); C07C 209/52 (2013.01); C07C 209/66 (2013.01); C07C 213/02 (2013.01); C07C 213/08 (2013.01); C07D 209/08 (2013.01); C07C 2101/14 (2013.01)

(58) Field of Classification Search
CPC ... C07C 209/08; C07C 209/50; C07C 209/52; C07C 209/66; C07C 209/26; C07C 213/08; C07C 213/02; B01J 31/00; C07B 43/04
See application file for complete search history.

(56) References Cited

PUBLICATIONS

International Search Report; PCT/EP2014/063343; International Filing Date: Jun. 25, 2014; 2 pgs.
Jacquet, Olivier et al.; C02 as a C1-Building Block for the Catalytic Methylation of Aminest; Chem. Sci., 2013,4, 2127-2131.
John A. Marsella and Guido P. Pez; Ruthenium-Catalyzed Formation of N-Methyl Formamides From Synthesis Gas and Ammonia; Journal of Molecular Catalysis, 36 (1986) 65-76.

*Primary Examiner* — Sun Jae Yoo
(74) *Attorney, Agent, or Firm* — Schmeiser, Olsen & Watts, LLP

(57) ABSTRACT

A method for the methylation of amines, amides and imines comprises the step of reacting these compounds with $CO_2$ and $H_2$ in the presence of a Ruthenium-phosphine complex.

9 Claims, No Drawings

METHOD FOR THE METHYLATION OF NITROGEN-CONTAINING ORGANIC COMPOUNDS

CROSS-REFERENCE TO RELATED APPLICATIONS

This application claims priority to PCT Application No. PCT/EP2014/063343, having a filing date of Jun. 25, 2014, based on EP 13175305.5, having a filing date of Jul. 5, 2013, the entire contents of which are hereby incorporated by reference.

FIELD OF TECHNOLOGY

The following relates to a method for the (reductive) N-methylation of nitrogen-containing organic compounds, especially amines, amides and imines.

BACKGROUND

The methylation of these compounds is synthetically interesting due to the importance of many of these compounds e.g. as bioactive compounds or pharmaceuticals. The conventional methods include alkylation reagents such as methyliodide or dimethylsulfate or the Eschweiler-Clark-reaction.

However, due to the significance of this reaction there is a constant need in the art for alternative methylation methods of nitrogen-containing organic compounds.

SUMMARY

An aspect relates to a method for the N-methylation of nitrogen-containing organic compounds, comprising the step of:
  a) reacting the nitrogen-containing organic compound with $CO_2$ and $H_2$ in the presence of a Ruthenium-Phosphine-complex The term "nitrogen-containing organic compound" in the sense of embodiments of the present invention especially means organic compounds which contain a nitrogen in the formal oxidation state (<0), e.g. primary and secondary amines, amides, imines and imides. Especially preferred—although not limiting—are aromatic amines, amides, imines and imides since it has been observed for many of these compounds that these are especially suitable for the inventive method.

$CO_2$ and/or $H_2$ are usually used as gases. However, this is not limiting and the reaction may also be used in applications where either $CO_2$ and/or $H_2$ are set free or (at least formally) made from precursor compounds or in reactions, including transfer hydrogenations. $CO_2$ can also be used as solvent, i.e. the $CO_2$ would be in liquid or near or supercritical form then.

The term "phosphine" in the sense of embodiments of the present invention especially means and/or includes trivalent phosphororganic compounds, especially compounds with the general formula $PR^1R^2R^3$, $R^1$ to $R^3$ being independent from each other an organic residue such as e.g. a substituted or unsubstituted alkyl, aryl and/or heteroaryl.

The term "Ruthenium-Phosphine-complex" especially means and/or includes a ruthenium complex where in the coordination sphere of the ruthenium a trivalent phosphororganic component is present so that a bond (may it be a covalent and/or a coordination bond) between the ruthenium and the trivalent phosphororganic component is formed at least temporarily during the reaction.

Surprisingly it has been found that by doing so it is possible to methylate the nitrogen-containing compound, using only $CO_2$ and $H_2$ as sources. It should be noted that in case the nitrogen-containing compound is an imine or amide, usually also reduction of the imino or amido-function to amines occurs. Therefore in these cases the method is a reductive N-methylation method.

For most applications within embodiments of the present invention, at least one of the following advantages could be observed:
  The reaction can be used on an industrial scale as well as on a small scale
  The reaction is easily adaptable to various applications and their demands
  The reaction tolerates many functional groups
  The reaction is atom-efficient, using $CO_2$ as carbon source It should be noted that the Ruthenium-Phosphine-complex may be used as a homogenous catalyst or in immobilized form. Also two-phase systems and phase-transfer-catalysis may be used depending on the actual application of embodiments of the invention. Besides a reaction in batch mode, also a continuous reaction system is possible.

It should furthermore be noted that the Ruthenium-Phosphine-complex may include other ligands such as (but not limited to) carbene, nitrogen containing-ligands such as amines or amides, phosphites, phosphoamidites, phosphoric ethers or esters, sulfides etc.

According to a preferred embodiment of the present invention, step a) is performed under acidic conditions. This has been shown to greatly increase the efficiency for most applications within embodiments of the present invention.

The term "acidic conditions" in the sense of embodiments of the present invention especially means and/or includes that during the reaction at least temporarily more acid than base is present.

According to a preferred embodiment the Phosphine in the Ruthenium-Phosphine-Complex is a Tri(hetero)aryl and/or Bi(hetero)arylalkyl-Phosphine. These compounds have proven themselves in practice.

Generic group definition: Throughout the description and claims generic groups have been used, for example alkyl, alkoxy, aryl. Unless otherwise specified the following are preferred groups that may be applied to generic groups found within compounds disclosed herein:
alkyl: linear and branched C1-C8-alkyl,
alkenyl: C2-C6-alkenyl,
cycloalkyl: C3-C8-cycloalkyl,
alkoxy: C1-C6-alkoxy,
alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1, 4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl,
aryl: selected from homoaromatic compounds having a molecular weight under 300,
arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene,
heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, Unless otherwise specified the following are more preferred group restrictions that may be applied to groups found within compounds disclosed herein:
alkyl: linear and branched C1-C6-alkyl,
alkenyl: C3-C6-alkenyl,
cycloalkyl: C6-C8-cycloalkyl,
alkoxy: C1-C4-alkoxy,
alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl,
aryl: selected from group consisting of: phenyl; biphenyl; naphthalenyl; anthracenyl; and phenanthrenyl,
arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene,
heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heteroarylene: selected from the group consisting of: pyridin 2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl.

According to a preferred embodiment of the present invention, the Ruthenium-Phosphine-Complex comprises more than one Phosphine, i.e. that in the coordination sphere of the ruthenium two or more trivalent phosphororganic components are present so that bonds (may it be covalent or coordination bonds) between the ruthenium and the phosphororganic components are formed at least temporarily during the reaction. Especially preferred are Ruthenium-Triphosphine-Complexes.

It should be noted that embodiments of the present invention are not limited to Ruthenium-Phosphine-Complexes where all phosphines are bound to the Ruthenium. Actually in many applications of embodiments of the present invention, the phosphine is used in excess so that also non-bound phosphines are present.

According to a preferred embodiment of the present invention, the Ruthenium-Phosphine-Complex comprises a bisphosphororganic component, trisphosphororganic component or a higher phosphororganic component. The term "bisphosphororganic component" and "trisphosphororganic component" in this context especially means and/or includes organic components in which two and three, respectively, trivalent phosphors are present. It should be noted that not necessarily all of the phosphines are bound to the Ruthenium during step a). Especially if higher phosphororganic components (in the sense of embodiments of the present invention organic compounds with more than three trivalent phosphors) are used, not all of the phosphors are catalytically involved in the reaction; nevertheless these compounds are preferred compounds within embodiments of the present invention as well.

Especially preferred in this context are phosphororganic components where the "bridging" moiety between the phosphors is an alkyl or alkylene moiety whereas the further ligands at the phosphor are aryl or heteroaryl. An especially preferred component in this context is Triphos=1,1,1-tris(diphenylphosphinomethyl)ethane, which has the following structure:

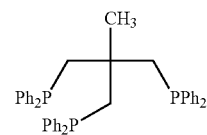

According to a preferred embodiment of the present invention, the Ruthenium-Phosphine-Complex comprises a bisphosphororganic component, trisphosphororganic component or a higher phosphororganic component which furthermore includes one or more donor moieties which can serve as ligands for the Ruthenium. Especially preferred in this context are carbenes, nitrogen containing-ligands such as amines or amides, sulfides, phosphites, phosphoamidites, phosphoric ethers or esters. These compounds have proven themselves in practice. Yet especially preferred are bisphosphororganic components with one further donor moiety.

It should be noticed that according to one preferred embodiment of the present invention, the Ruthenium-Phosphine-complex may (prior to the reaction) comprise one or more "volatile" or easy removable ligand which stabilizes the complex so that it may be handled before the reaction but during the reaction sequence is replaced by the reactants. Suitable ligands are i.e. trimethylmethane, cyclopentadienyl, allyl, methylallyl, ethylene, cyclooctadiene, acetylactonate, acetate or carbon monoxide.

According to a preferred embodiment of the present invention, step a) is performed under acidic conditions whereby the (initial) concentration of acid is ≥0.5 times the concentration of Ruthenium (in mol:mol). It has been found that by doing so the reaction speed and the TON can be increased for many applications within embodiments of the present invention. More preferred the concentration of acid is ≥0.8 to ≤20 times the concentration of Ruthenium (in mol:mol), yet more preferred ≥1 to ≤10 times.

According to a preferred embodiment of the present invention, step a) is performed under acidic conditions whereby the acid is selected out of the group comprising organic or inorganic acids, especially sulfonic acids, especially methanesulfonic acid, trifluormethansulfonic acid, p-toluolsulfonic acid, p-bromobenzosulfonic acid, p-nitrobenzosulfonic acid, sulfuric acid, hydrochloric acid, hydrofluoric acid, trifluoracetic acid, perchloric acid or mixtures thereof. Even more preferred are acids which provide weak coordinating anions after deprotonation, such as bis(trifluoromethane)sulfonimide or mixtures thereof with aforementioned acids. These compounds have proven themselves in practice.

According to a preferred embodiment of the present invention, step a) is carried out at a temperature of ≥0° C. to ≤200° C., preferably ≥20° C. to ≤190° C., more preferred ≥60° C. to ≤180° C., even more preferred ≥100° C. to ≤170° C. and most preferred at ≥120° C. to ≤160° C. This has been shown to be most efficient for most applications within embodiments of the present invention.

According to a preferred embodiment of the present invention, step a) is carried out in a dipolar protic or aprotic solvent or in $CO_2$ (either liquid or near or supercritical). Preferred solvents are ethers, cyclic ethers (such as THF or dioxane) and $CO_2$.

According to a preferred embodiment of the present invention, step a) is carried out at an initial $H_2$ pressure of ≥1 bar, preferably ≥10 bar, yet preferred ≥20 bar, most preferred ≥60 bar. This has been shown to greatly increase the reaction speed and efficiency for most applications of embodiments of the present invention.

According to a preferred embodiment of the present invention, step a) is carried out at an initial $CO_2$ pressure of ≥1 bar, preferably ≥10 bar, yet preferred ≥20 bar. This has been shown to greatly increase the reaction speed and efficiency for most applications of embodiments of the present invention.

In case that the nitrogen-containing organic compound is an amide, it is especially preferred that step a) is carried out at an initial $CO_2$ pressure of ≥30 bar, yet preferred ≥40 bar. It has been observed that under these conditions the side-reaction of decarbonylation (which may occur with some amides) can be suppressed or greatly reduced.

According to a preferred embodiment of the present invention, the initial pressure ratio of $H_2:CO_2$ is ≥0.5:1 to ≤5:1, more preferably ≥1:1 to ≤4:1 and most preferred ≥1.5:1 to ≤3:1. This has been shown to greatly increase the reaction speed and efficiency for most applications of embodiments of the present invention.

According to a preferred embodiment of the present invention, the method furthermore comprises a step a0) to be performed before step a):

a0) Reacting suitable precursor compounds to form the Ruthenium-Phosphine-Complex Suitable Ruthenium-containing precursor compounds include $Ru(acac)_3$, $[Ru(cod)(methylallyl)_2]$ $Ru(nbd)(methylallyl)_2$, $Ru(ethylene)2(methylallyl)_2$.

Step a0) may be carried out at room temperature or at the same temperature at step a).

The aforementioned components, as well as the claimed components and the components to be used in accordance with embodiments of the invention in the described embodiments, are not subject to any special exceptions with respect to their size, shape, material selection and technical concept such that the selection criteria known in the pertinent field can be applied without limitations.

Additional details, characteristics and advantages of the object of embodiments of the invention are disclosed in the subclaims and the following description of the respective Examples which are for illustration of embodiments of the invention only and non-binding.

EXAMPLES

Synthesis of [Ru(Triphos)(TMM)]

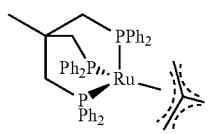

A 35 mL schlenk tube was charged with 159.5 mg (0.5 mmol) [Ru(cod)(methylallyl)$_2$] and 312.0 mg 1,1,1-tris(diphenylphosphinomethyl)ethane (Triphos) in 25 mL toluene. After heating for 2 h at 110° C., the resulting solution was concentrated in vacuo and treated with 10 mL of pentane. The precipitating complex was isolated and washed three times with 10 mL pentane. After drying, [Ru(Triphos)(TMM)] was obtained as a bright yellow powder in 75% yield.

General procedures for direct methylation of amines with $CO_2/H_2$.

All high pressure batch experiments were conducted in stainless steel 10 mL autoclaves equipped with a glass inlet and a magnetic stir bar. Prior to use, the autoclave was dried under vacuum for 3 hours and repeatedly filled with argon. Under an argon atmosphere, catalyst [Ru(Triphos)(TMM)] (0.019 g, 0.025 mmol) and HNTf$_2$ (0.014 g, 0.05 mmol) were weighed in a Schlenk tube. After dissolving in THF (1.0 mL), the mixture was transferred viaqa cannula to the autoclave followed by the addition of the aniline substrate (1.0 mmol) in THF (1.0 mL). The autoclave was then pressurized with $CO_2$ to 20 bar and then $H_2$ was added up to a total pressure of 80 bar. The reaction mixture was stirred and heated to 150° C. in an oil bath. After 10 h, the autoclave was cooled in an ice bath and then carefully vented. The reaction solution was analyzed by $^1$H-NMR with internal standard mesitylene and the results confirmed by gas chromatography using dodecane as internal standard.

Example I

Methylation of N-methylaniline to N,N-Dimethylaniline

The reaction was carried out as described above, except where indicated. The results are shown in the following Table I:

TABLE I

| Entry | Acid [mol %] | Temp [° C.] | Time [h] | Yield [%] |
|---|---|---|---|---|
| 1 | — | 140 | 10 | 2 |
| 2 | HNTf$_2$ (0.5) | 140 | 22 | 11 |
| 3 | HNTf$_2$ (2.5) | 140 | 22 | 84 |
| 4 | HNTf$_2$ (5), no catalyst added | 140 | 22 | 0 |
| 5 | HNTf$_2$ (5), 1% catalyst used | 140 | 10 | 50 |
| 6 | HNTf$_2$ (5) | 140 | 22 | 97 |
| 7 | HNTf$_2$ (5), CO$_2$/H$_2$: (10/30 bar) | 140 | 22 | 25 |
| 8 | HNTf$_2$ (5) | 120 | 22 | 81 |
| 9 | HNTf$_2$ (5) | 100 | 22 | 58 |
| 10 | HNTf$_2$ (5) | 150 | 0.5 | 9 |
| 11 | HNTf$_2$ (5) | 150 | 1 | 20 |
| 12 | HNTf$_2$ (5) | 150 | 1.5 | 29 |
| 13 | HNTf$_2$ (5) | 150 | 2 | 34 |
| 14 | HNTf$_2$ (5) | 150 | 3 | 49 |
| 15 | HNTf$_2$ (5) | 150 | 4 | 69 |
| 16 | HNTf$_2$ (5) | 150 | 8 | 97 |
| 17 | HNTf$_2$ (5) | 150 | 10 | 99 |
| 18 | MSA (5) | 150 | 10 | 95 |
| 19 | p-TsOH (5) | 150 | 10 | 97 |

Example II

Methylation of Various Secondary Amines

The following amides were reacted as described above, using the following conditions: Substituted aromatic amine (1.0 mmol), [Ru(Triphos)(TMM)] (2.5 mol %), HNTf$_2$ (5 mol %), THF (2 mL), CO$_2$/H$_2$ (20/60 bar), 150° C. Results are shown in the following Table II:

TABLE II

| Entry | Amine | Product | Time [h] | Yield [%] |
|---|---|---|---|---|
| 1 | 3-fluoro-N-methylaniline | 3-fluoro-N,N-dimethylaniline | 22 | 90 |
| 2 | 4-chloro-N-methylaniline | 4-chloro-N,N-dimethylaniline | 10 | 90 |
| 3 | 4-methoxy-N-methylaniline | 4-methoxy-N,N-dimethylaniline | 10 | 35 |
| 4 | indoline | N-methylindoline | 20 | 73 |
| 5 | indole | N-methylindoline | 20 | 70 |
| 6 | N-cyclohexylaniline | N-cyclohexyl-N-methylaniline | 15 | 64 |
| 7 | diphenylamine | N-methyldiphenylamine | 48 | 27 |

Example III

Methylation of Various Primary amines and Amides

Several primary amines and Acetanilide were reacted using the following conditions: Substituted primary aniline or amide (1.0 mmol), [Ru(Triphos)(TMM)] (2.5 mol %), HNTf$_2$ (5 mol %), THF (2 mL), CO$_2$/H$_2$ (20/60 bar), 150° C. The results are shown in the following Table III

TABLE III

| Entry | amine/amide | Product | Time [h] | Yield [%] |
|---|---|---|---|---|
| 1 | aniline | N,N-dimethylaniline | 15 | 94 |
| 2 | 4-chloroaniline | 4-chloro-N,N-dimethylaniline | 10 | 93 |
| 3 | 2-fluoroaniline | 2-fluoro-N,N-dimethylaniline | 24 | 93 |

TABLE III-continued

| Entry | amine/amide | Product | Time [h] | Yield [%] |
|---|---|---|---|---|
| 4 | F₃C-C₆H₃(CH₃)-NH₂ | F₃C-C₆H₃(CH₃)-N(CH₃)₂ | 20 | 94 |
| 5 | 2,4,6-trimethylaniline | N,N-dimethyl-2,4,6-trimethylaniline | 15 | 84 |
| 6 | acetanilide | N-ethyl-N-phenyl | 24 | 69 |

Example IV

Reductive Methylation of Various Imines

Several imines were reacted using the following conditions: Substituted imine (1.0 mmol), [Ru(Triphos)(TMM)] (2.5 mol %), HNTf₂ (5 mol %), THF (2 mL), $CO_2/H_2$ (20/60 bar), 100° C. The results are shown in the following Table IV

TABLE IV

| Entry | Imine | Product | Time [h] | Yield [%] |
|---|---|---|---|---|
| 1 | MeO-C₆H₄-N=C(CH₃)-C₆H₄-Cl | MeO-C₆H₄-N(CH₃)-CH(CH₃)-C₆H₄-Cl | 24 | 90 |
| 2 | MeO-C₆H₄-N=C(CH₃)-C₆H₅ | MeO-C₆H₄-N(CH₃)-CH(CH₃)-C₆H₅ | 24 | 80 |
| 3 | C₆H₅-N=C(CH₃)-naphthyl | C₆H₅-N(CH₃)-CH(CH₃)-naphthyl | 24 | 96 |

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method for the N-methylation of nitrogen-containing compounds comprising the step of:
   a) reacting the nitrogen-containing organic compound with $CO_2$ and $H_2$ in the presence of a Ruthenium-Phosphine-complex.

2. The method according to claim 1, wherein step a) is performed under acidic conditions.

3. The method according to claim 1, wherein the Phosphine in the Ruthenium-Phosphine-Complex is a Trisaryl, Trisheteroaryl, Bisarylalkyl and/or Bisheteroarylalkyl Phosphine.

4. The method according to one of claims 1, wherein the Ruthenium-Phosphine-Complex comprises a bisphosphororganic component, trisphosphororganic or higher phosphororganic component.

5. The method according to claim 1, wherein step a) is performed under acidic conditions whereby the acid is selected out of the group comprising sulfonic acids, especially methanesulfonic acid, trifluormethansulfonic acid, p-toluolsulfonic acid, p-bromobenzosulfonic acid, p-nitrobenzosulfonic acid, sulfuric acid, hydrochloric acid, hydrofluoric acid, trifluoracetic acid, perchloric acid, bis(trifluoromethane)sulfonimide or mixtures thereof.

6. The method according to claim 1, wherein step a) is carried out at an initial hydrogen pressure of ≥1 bar.

7. The method according claim 1, wherein step a) is carried out at an initial $CO_2$ pressure of ≥1 bar.

8. The method according to claim 1, wherein the initial pressure ratio of $H_2$: $CO_2$ is ≥0.5:1 to ≤5:1.

9. The method according to claim 1, wherein step a) is carried out in a dipolar protic or aprotic solvent or in $CO_2$.

* * * * *

UNITED STATES PATENT AND TRADEMARK OFFICE
CERTIFICATE OF CORRECTION

PATENT NO. : 9,650,310 B2
APPLICATION NO. : 14/902704
DATED : May 16, 2017
INVENTOR(S) : Jürgen Klankermayer et al.

Page 1 of 1

It is certified that error appears in the above-identified patent and that said Letters Patent is hereby corrected as shown below:

In the Claims

Column 10, Line 18 Claim 4, change "to one of claims 1" to -- to claim 1 --

Signed and Sealed this
Fifth Day of September, 2017

Joseph Matal
*Performing the Functions and Duties of the*
*Under Secretary of Commerce for Intellectual Property and*
*Director of the United States Patent and Trademark Office*